United States Patent [19]

Thim et al.

[11] Patent Number: 5,783,416
[45] Date of Patent: Jul. 21, 1998

[54] HUMAN SPASMOLYTIC POLYPEPTIDE IN GLYCOSYLATED FORM

[75] Inventors: Lars Thim, Gentofte; Kjeld Norris; Fanny Norris, both of Hellerup; Søren Erik Bjørn, Lyngby; Mogens Christensen, Gentofte; Per Franklin Nielsen, Vrløse, all of Denmark

[73] Assignee: Novo Nordisk A/S, Bagsvaerd, Denmark

[21] Appl. No.: 491,976

[22] PCT Filed: Jan. 20, 1994

[86] PCT No.: PCT/DK94/00037

§ 371 Date: Aug. 2, 1995

§ 102(e) Date: Aug. 2, 1995

[87] PCT Pub. No.: WO94/17102

PCT Pub. Date: Aug. 4, 1994

[30] Foreign Application Priority Data

Jan. 21, 1993 [DK] Denmark ................. 0068/93

[51] Int. Cl.⁶ ............ C12N 15/63; C12N 1/15; A61K 38/17; C07K 14/47
[52] U.S. Cl. ........... 435/69.1; 435/71.1; 435/254.11; 435/254.21; 435/254.3; 514/8; 530/395
[58] Field of Search ................. 435/69.1, 71.1, 435/254.11, 254.21, 254.3; 514/8; 530/395

[56] References Cited

U.S. PATENT DOCUMENTS 4,370,317  1/1983  Jorgensen et al. .................. 514/12

FOREIGN PATENT DOCUMENTS

| 0385308 A1 | 9/1990 | European Pat. Off. |
| 3808456 A1 | 9/1989 | Germany. |
| 92/14837 A1 | 9/1992 | WIPO. |
| 94/17102 A1 | 8/1994 | WIPO. |

OTHER PUBLICATIONS

Playford et al. Human spesmolytic polypeptide is a cytoprotective agent that stimulates cell migration. Gastroenterology. vol. 199, pp. 108–116, 1995.

Abstract –Thim et al. Biochim Biophys Acta (Netherlands) 827:(3) pp. 410–418 (1985).

Tomasetto et al., The EMBO Journal vol. 9, No. 2 pp. 407–414 (1990).

Bowie et al. Deciphering the message in protein sequences: tolerance to amino acid substitutions. Science. vol. 247, pp. 1306–1310, Mar. 16, 1990.

Carr. H NMR-based determination of the secondary structure of porcine pancreatic spasmolytic polypeptide: one of a new family of "trefoil" motif containing cell growth factors. Biochemistry. vol. 31, No. 7, pp. 1998–2004, 1992.

Hitzeman et al. Use of heterologous and homologous signal sequences for secretion of heterologous proteins from yeast. In: Methods in Enzymology. Academic Press, Inc., NY. vol. 185, pp. 421–440, 1990.

Hoffman. A new repetitive protein from Xenopus laevis skin highly homologous to pancreatic spasmolytic polypeptide. The Journal of Biological Chemistry. vol. 263, No. 16, pp. 7686–7690, Jun. 5, 1988.

Jorgensen et al. Pancreatic spasmolytic polypeptide: I. Preparation and initial chemical characterization of a new polypeptide from porcine pancreas. Regulatory Peptides. vol. 3, pp. 207–219, 1982.

Primary Examiner—Elizabeth C. Kemmerer
Assistant Examiner—Brian Lathrop
Attorney, Agent, or Firm—Steve T. Zelson, Esq.; Valeta A. Gregg, Esq.

[57] ABSTRACT

A human spasmolytic polypeptide (HSP) having the amino acid of SEQ ID NO:1, characterized by being in a glycosylated form.

17 Claims, 10 Drawing Sheets

Trefoil family of peptides

| Peptide | | Number of trefoil domains | Species |
|---|---|---|---|
| Intestinal Trefoil Factor | (ITF) |  | Rat Human |
| Breast cancer associated peptide | (pS2) |  | Human |
| Spasmolytic polypeptide | (hSP) (PSP) (mSP) |  | Human Porcine Mouse |
| Spasmolysins | (xP1) |  | Frog |
| | (xP4) |  | Frog |

FIG. 1  Trefoil family of peptides
| Peptide | | Number of trefoil domains | Species |
|---|---|---|---|
| Intestinal Trefoil Factor | (ITF) | 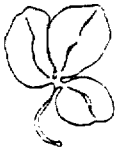 | Rat<br>Human |
| Breast cancer associated peptide | (pS2) | 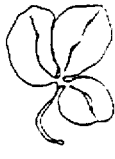 | Human |
| Spasmolytic polypeptide | (hSP)<br>(PSP)<br>(mSP) |  | Human<br>Porcine<br>Mouse |
| Spasmolysins | (xP1) | 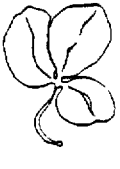 | Frog |
| | (xP4) | 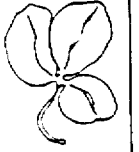 | Frog |

```
EcoRI
GAATTCCATTCAAGAATAGTTCAAACAAGAAGATTACAAACTATCAATTTCATACACAAT

ATAAACGACCAAAAGAATGAAGGCTGTTTTCTTGGTTTTGTCCTTGATCGGATTCTGCTG
              M  K  A  V  F  L  V  L  S  L  I  G  F  C  W

GGCCCAACCAGTCACTGGCGATGAATCATCTGTTGAGATTCCGGAAGAGTCTCTGATCAT
 A  Q  P  V  T  G  D  E  S  S  V  E  I  P  E  E  S  L  I  I

CGCTGAAAACACCACTTTGGCTAACGTCGCCATGGCTGAGAGATTGGAGAAGAGAgagaa
 A  E  N  T  T  L  A  N  V  A  M  A  E  R  L  E  K  R  E  K
                                    Dde I      1
accctcccctgccagtgctccaggcTGAGCCCCCATAACAGGACGAACTGCGGCTTCCC
 P  S  P  C  Q  C  S  R  L  S  P  H  N  R  T  N  C  G  F  P TGGAATCACCAGTGACCAGTGTTTTGACAATGGATGCTGTTTCGACTCCAGTGTCACTGG
 G  I  T  S  D  Q  C  F  D  N  G  C  C  F  D  S  S  V  T  G
AvaII       2                                       4
Ggtcccctggtgtttccacccccctcccaaagcaagagtcggatcagtgccctcatggaggt
 V  P  W  C  F  H  P  L  P  K  Q  E  S  D  Q  C  V  M  E  V
Dde I
cTCAGACAGAAGAAACTGTGGCTACCCGGGCATCAGCCCCGAGGAATGCGCCTCTCGGAA
 S  D  R  R  N  C  G  Y  P  G  I  S  P  E  E  C  A  S  R  K
                           5       NcoI
GTGCTGCTTCTCCAACTTCATCTTTGAAGTGCCatggtgcttcttcccgaactctgtgga
 C  C  F  S  N  F  I  F  E  V  P  W  C  F  F  P  N  S  V  E
              XbaI
agactgccattactaagtCTAGA
 D  C  H  Y
```

FIG. 3

HUMAN SPASMOLYTIC POLYPEPTIDE IN GLYCOSYLATED FORM

CROSS-REFERENCE TO RELATED APPLICATIONS

This application is filed under 35 USC 371 as the national stage of International Application PCT/DK94/00037 filed Jan. 20, 1994, which is incorporated herein by reference.

FIELD OF INVENTION

The present invention relates to human spasmolytic polypeptide in glycosylated form, variants of human and porcine spasmolytic polypeptides and a method of producing spasmolytic polypeptides in glycosylated form.

BACKGROUND OF THE INVENTION

Human spasmolytic polypeptide (HSP) belongs to a family of peptides containing one or more characteristic trefoil domains [1]. The trefoil domain is made up of a sequence of 38 or 39 amino acid residues in which 6 cystein residues are linked in the configuration 1–5, 2–4 and 3–6 thus forming a characteristic trefoil structure [1]. The trefoil family of peptides consists of rat intestinal trefoil factor, ITF [2], human breast cancer associated peptide, pS2 [3,4,5], porcine, human and murine spasmolytic polypeptide (PSP, HSP, MSP) [6,7,8] and frog spasmolysins (xP1, xP2 and xP4) [8,10,11] all containing 1, 2 or 4 trefoil domains (FIG. 1).

The physiological function of the trefoil peptides is poorly understood, and so far only PSP has been studied in any detail. In the porcine pancreas, PSP is found in the acinar cells and to be secreted in large amounts (50–100 mg/ml) into the pancreatic juice upon stimulation with pancreozymin or secretin [12,13,14]. PSP is resistant to digestion by intestinal proteases in the gastrointestinal tract [12], and specific binding of PSP to rat intestinal mucosa cells and membrane preparations from these cells has been demonstrated [15,163. In the porcine gastrointestinal tract, specific receptor-like binding to Paneth cells in the duodenum has been found [17]. These results suggest a unique intraluminal function of the peptide. A pharmacological screening has indicated that PSP has spasmolytic and gastric acid secretion inhibitory effects [18], and studies on mammalian cells have indicated a growth factor-like activity of PSP [19].

The DNA sequence and derived amino acid sequence of the human counterpart of porcine SP is shown in [8]. Unlike PSP, human SP (FIG. 2), has been found to be expressed in the stomach, but not in the pancreas to any greater extent [8]. An increased expression of HSP and pS2 has been reported to be associated with peptic ulcers and mucosal injury in inflammatory bowel disease [20,21] indicating a possible healing function of these peptides.

Only very limited amounts of HSP can be prepared by extraction of human tissue. An object of study resulting in the present invention was therefore to prepare recombinant HSP in sufficient amounts for physiological and biochemical studies of the peptide.

SUMMARY OF THE INVENTION

It has surprisingly been found that when recombinant HSP is produced in certain host organisms, a proportion of it is produced in glycosylated form by posttranslational modifications. The glycosylated form of HSP has not, to applicant's best knowledge, been described previously.

Accordingly, the present invention relates to human spasmolytic polypeptide (HSP) which has the amino acid sequence

```
Glu Lys Pro Ser Pro Cys Gln Cys Ser Arg Leu Ser Pro His Asn
Arg Thr Asn Cys Gly Phe Pro Gly Ile Thr Ser Asp Gln Cys
Phe Asp Asn Gly Cys Cys Phe Asp Ser Ser Val Thr Gly Val
Pro Trp Cys Phe His Pro Leu Pro Lys Gln Glu Ser Asp Gln
Cys Val Met Glu Val Ser Asp Arg Arg Asn Cys Gly Tyr Pro
Gly Ile Ser Pro Glu Glu Cys Ala Ser Arg Lys Cys Cys Phe Ser
Asn Phe Ile Phe Glu Val Pro Trp Cys Phe Phe Pro Asn Ser Val
Glu Asp Cys His Tyr                    (SEQ ID NO:1)
``` or a functionally equivalent homologue thereof, characterized by being in glycosylated form.

In the present context, the term "functionally equivalent" is intended to indicate that the homologous polypeptide has a biological activity (e.g. spasmolytic effect) corresponding to that of native HSP. The term "homologue" is intended to indicate a polypeptide encoded by DNA which hybridizes to the same probe as the DNA coding for HSP under conditions of high or low stringency (e.g. as described in Sambrook et. al., *Molecular Cloning: A Laboratory Manual*, 2nd Ed., Cold Spring Harbor Laboratory Press, Cold Spring Harbor, N.Y., 1989). More specifically, the term is intended to refer to a DNA sequence which is at least 60% homologous to the sequence encoding HSP with the amino acid sequence shown above. The term is intended to include modifications of the DNA sequence such as nucleotide substitutions which do not give rise to another amino acid sequence of the polypeptide, but which correspond to the codon usage of the host organism into which the DNA construct is introduced or nucleotide substitutions which do give rise to a different amino acid sequence and therefore, possibly, a different protein structure which might give rise to a mutant polypeptide with different properties than the native enzyme. Other examples of possible modifications are insertion of one or more codons into the sequence, addition of one or more codons at either end of the sequence, or deletion of one or more codons at either end or within the sequence. The term "glycosylated" is intended to indicate that a carbohydrate moiety is present at one or more sites of the protein molecule.

It is at present contemplated that glycosylation of HSP may give rise to differences in the biological activity of the protein, for instance with respect to stability towards proteolytic enzymes in the gastrointestinal tract, solubility at gastric and/or intestinal pH compared to non-glycosylated HSP, antigenicity, half-life, tertiary structure, and targeting to receptors on appropriate cells.

In another aspect, the present invention relates to a variant of a spasmolytic polypeptide (SP) which is a fragment of human spasmolytic polypeptide (HSP) or porcine spasmolytic polypeptide (PSP) comprising at least one trefoil domain.

The variant SP may be provided in both glycosylated and non-glycosylated form. It is at present contemplated that such a variant may be advantageous to use instead of full-length SP because of a higher specific biological activity, increased solubility and stability, longer half-life, easier way of production, or the like.

It is assumed that other spasmolytic polypeptides than HSP will, if provided with a glycosylation site, also be expressed in predominantly glycosylated form. In a further aspect, the present invention therefore relates to a method of preparing a spasmolytic polypeptide in at least 60% glycosylated form, wherein a host cell transformed with a DNA fragment encoding a spasmolytic polypeptide and capable of providing glycosylation of said spasmolytic polypeptide is

3 cultured under conditions permitting production of said spasmolytic polypeptide and recovering the resulting spasmolytic polypeptide from the culture.

BRIEF DESCRIPTION OF THE DRAWINGS

The invention is further illustrated in the following example with reference to the appended drawings in which FIG. 1 shows the trefoil family of peptides. Intestinal trefoil factor (ITF) contains one trefoil domain [2], as does the breast cancer associated pS2 peptide [3,4]. The spasmolytic polypeptides from man, pig and mouse contain two trefoil domains [1,8]. Spasmolysins from *Xenopus laevis* contain one or four trefoil domains [10]. Recently, a member of the frog trefoil family containing two domains has been described [11].

FIG. 3 shows the nucleotide sequence (SEQ ID NO:2) and corresponding amino acid sequence (SEQ ID NO: 3) of the 563 bp EcoRI—XbaI fragment encoding the leader—HSP fusion protein. The Kex 2 processing site is indicated by a vertical arrow. The leader and the PCR cloned parts of the HSP gene are shown in capital letters, while the synthetic parts are shown i small letters. The underlined sequences correspond to the PCR primers with horizontal arrows indicating the direction. Restriction sites relevant for the construction are shown.

DETAILED DESCRIPTION OF THE INVENTION

Figure 2:
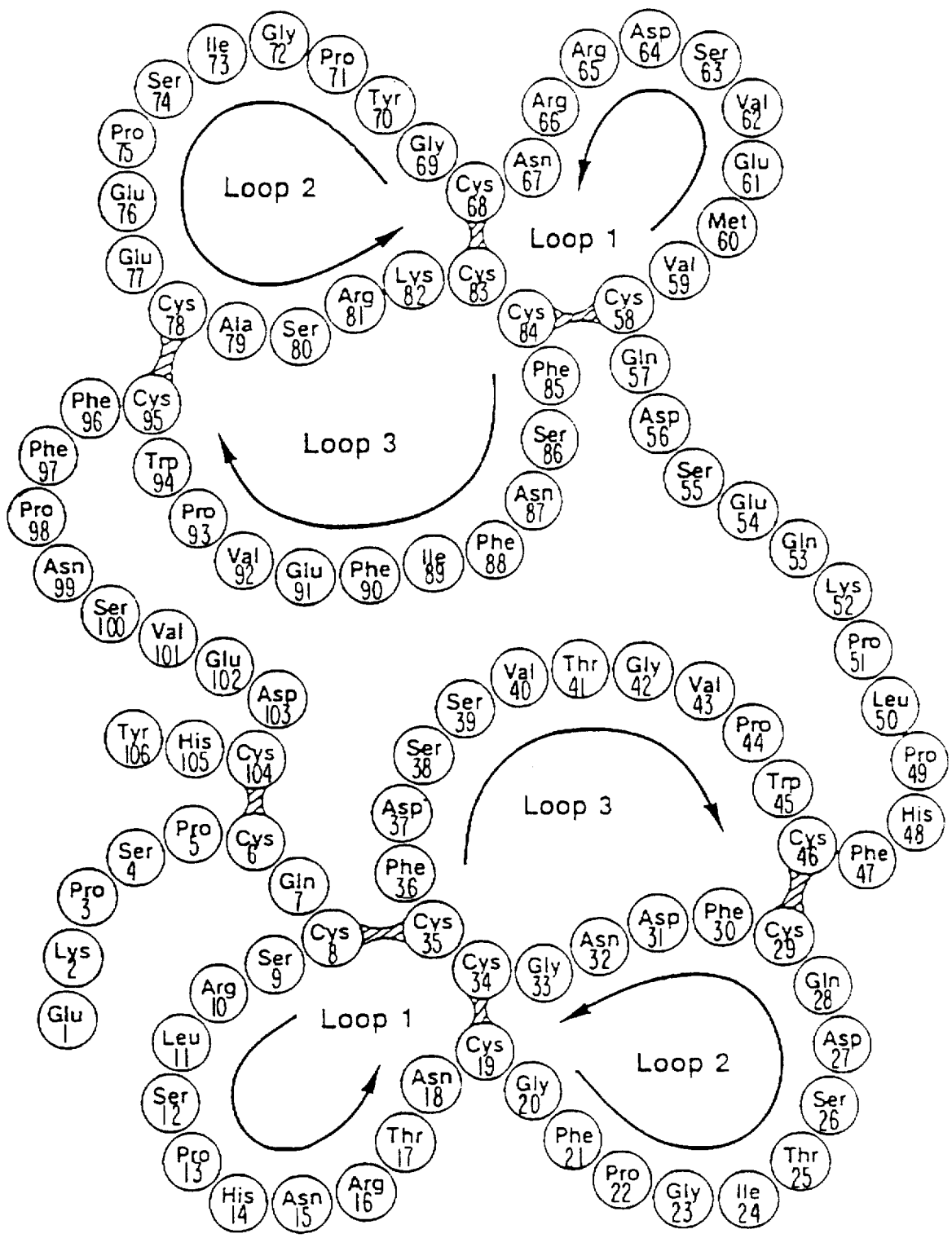
FIG. 2 shows the proposed structure of human spasmolytic polypeptide, HSP(SEQ ID NO:1). The primary amino acid sequence is taken from Tomasetto et al. [8], and the disulphide bonds are placed in homology to PSP [1].

It has been found that, at least when recombinant HSP is produced in yeast, the proportion of it that is provided in glycosylated form is in N-glycosylated form. It has further been found that glycosylation takes place at Asn15 of the sequence shown above. In preferred embodiments of glycosylated HSP, the glycosylated side chain contains at least one hexose unit. In particular, the glycosylated side chain may contain at least one mannose unit, preferably at least five mannose units, most preferably at least ten mannose units. In one preferred embodiment of glycosylated HSP of the invention, the glycosylated side chain contains 13–17 mannose units. In other preferred embodiments, the glycosylated HSP is in addition glycosylated with at least one unit of N-acetyl glucosamine (GlcNAc). In the currently preferred embodiment, the glycosylated HSP is glycosylated at Asn15 with $(GlcNAc)_2(Man)_{10-15}$.

It is further contemplated to produce homologues of HSP which are provided with one or more additional glycosylation sites. Thus, the present invention also relates to HSP homologues, wherein Lys2 is replaced by Asn, Gln7 is replaced by Asn, Arg10 is replaced by Asn, Gly 20 is replaced by Thr or Ser, Gly23 is replaced by Asn, Ile 24 is replaced by Asn, Phe 36 is replaced by Asn, Asp 37 is replaced by Asn, Ser39 is replaced by Asn, Gln53 is replaced by Asn, Glu61 is replaced by Asn, Asp64 is replaced by Asn, Arg66 is replaced by Thr or Ser, Gly69 is replaced by Thr or Ser, Gly72 is replaced by Asn, Ile89 is replaced by Thr or Ser, Pro98 is replaced by Asn or Val101 is replaced by Thr or Ser, or a combination of two or more of these substitutions. In a currently preferred embodiment of such an HSP homologue, Asp64 is replaced by Asn, and Arg66 is replaced by Thr or Ser.

It is of course understood that HSP homologues of the invention may be glycosylated in the same manner at one or more of these sites as described above for glycosylation at Asn15.

It is assumed that the trefoil structure common among spasmolytic polypeptides is important for the function of HSP and PSP. The variant human or porcine SP comprising a fragment of the full-length polypeptide should therefore include at least three disulfide bonds to provide this structure. Consequently, the variant may comprise at least a sequence of amino acids from position 8 to 46 or from position 58 to 95, each of which sequences defines a trefoil domain of HSP and PSP.

As indicated above, the SP variant of the invention may be provided in non-glycosylated form. This may, for instance, be accomplished by substituting Asn15 by another amino acid, e.g. Asp or Glu, or by substituting Thr17 by another amino acid except Ser, e.g. Ala. It is more likely, however, that one or more additional glycosylation sites will be introduced into this domain, for instance by replacing Arg10 by Asn, Gly 20 by Thr or Ser, Gly23 by Asn, ILe24 by Asn, Phe36 by Asn, Asp37 by Asn, or Ser39 by Asn, or a combination of two or more of these substitutions.

On the other hand, it may be desirable to provide the trefoil domain from position 58 to 95 with a glycosylation site lacking in this domain in native HSP and PSP. Thus, Glu61 may be replaced by Asn, Asp64 by Asn, Arg66 by Thr or Ser, Gly69 by Thr or Ser, or Gly72 is replaced by Asn, or a combination of two or more of these substitutions. In a currently preferred embodiment of the variant, Asp64 is replaced by Asn, and Arg66 is replaced by Thr or Ser.

It is of course understood that variants of the invention may be glycosylated in the same manner at one or more of these sites as described above for glycosylation at Asn15 in full-length HSP.

A DNA sequence encoding HSP may suitably be isolated from a human genomic DNA library by PCR (polymerase chain reaction) cloning using primers based on the published cDNA sequence [8]. Alternatively, the DNA sequence may be prepared synthetically by established standard methods, e.g. the phosphoamidite method described by S. L. Beaucage and M. H. Caruthers, *Tetrahedron Letters* 22, 1981, pp. 1859–1869, or the method described by Matthes et al., *EMBO Journal* 3, 1984, pp. 801–805. According to the phosphoamidite method, oligonucleotides are synthesized, e.g. in an automatic DNA synthesizer, purified, annealed, ligated and cloned in suitable vectors. The cDNA sequence shown in [8] may be used as the basis of oligonucleotide synthesis.

Alternatively, it is possible to use cDNA coding for HSP obtained by screening a human cDNA library with oligonucleotide probes in accordance with well-known procedures.

Furthermore, the DNA sequence may be of mixed synthetic and genomic, mixed synthetic and cDNA or mixed genomic and cDNA origin prepared by ligating fragments of genomic, synthetic or cDNA origin (as appropriate), the fragments corresponding to various parts of the entire DNA sequence, in accordance with standard techniques.

The SP variant of the invention may be encoded by a fragment of the full-length DNA sequence, prepared by one of the methods indicated above, or by suitably truncating the full-length sequence.

The DNA sequence encoding HSP or an SP variant of the invention may then be inserted in a suitable expression vector. The recombinant expression vector may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding HSP or an SP variant of the invention should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA encoding the inhibitor of the invention in mammalian cells are the SV 40 promoter (Subramani et al., *Mol. Cell Biol.* 1, 1981, pp. 854–864), the MT-1 (metallothionein gene) promoter (Palmiter et al., *Science* 222, 1983, pp. 809–814) or the adenovirus 2 major late promoter. Suitable promoters for use in yeast host cells include promoters from yeast glycolytic genes (Hitzeman et al., *J. Biol. Chem.* 255, 1980, pp. 12073–12080; Alber and Kawasaki, *J. Mol. Appl. Gen.* 1, 1982, pp. 419–434) or alcohol dehydrogenase genes (Young et al., in *Genetic Engineering of Microorganisms for Chemicals* (Hollaender et al, eds.), Plenum Press, New York, 1982), or the TPI1 (U.S. Pat. No. 4,599,311) or ADH2-4c (Russell et al., *Nature* 304, 1983, pp. 652–654) promoters. Suitable promoters for use in filamentous fungus host cells are, for instance, the ADH3 promoter (McKnight et al., *The EMBO J.* 4, 1985, pp. 2093–2099) or the tpiA promoter.

The DNA sequence encoding HSP or an SP variant may also be operably connected to a suitable terminator, such as the human growth hormone terminator (Palmiter et al., op. cit.) or (for fungal hosts) the TPI1 (Alber and Kawasaki, op. cit.) or ADH3 (McKnight et al., op. cit.) promoters. The vector may further comprise elements such as polyadenylation signals (e.g. from SV 40 or the adenovirus 5 Elb region), transcriptional enhancer sequences (e.g. the SV 40 enhancer) and translational enhancer sequences (e.g. the ones encoding adenovirus VA RNAs).

The recombinant expression vector may further comprise a DNA sequence enabling the vector to replicate in the host cell in question. An examples of such a sequence (when the host cell is a mammalian cell) is the SV 40 origin of replication, or (when the host cell is a yeast cell) the yeast plasmid 2 μ replication genes REP 1–3 and origin of replication. The vector may also comprise a selectable marker, e.g. a gene the product of which complements a defect in the host cell, such as the gene coding for dihydrofolate reductase (DHFR) or one which confers resistance to a drug, e.g. neomycin, hygromycin or methotrexate, or the *Schizosaccharomyces pombe* TPI gene (described by P. R. Russell, *Gene* 40, 1985, pp. 125–130).

The procedures used to ligate the DNA sequences coding for HSP or the SP variant, the promoter and the terminator, respectively, and to insert them into suitable vectors containing the information necessary for replication, are well known to persons skilled in the art (cf., for instance, Sambrook et al., *Molecular Cloning: A Laboratory Manual*, Cold Spring Harbor, N.Y., 1989).

The host cell into which the expression vector is introduced may be any cell which is capable of producing the inhibitor of the invention and is preferably a eukaryotic cell, such as a mammalian, yeast or fungal cell.

The yeast organism used as the host cell may be any yeast organism which, on cultivation, produces large quantities of the inhibitor of the invention. Examples of suitable yeast organisms are strains of the yeast species *Saccharomyces cerevisiae*, *Saccharomyces kluyveri*, *Schizosaccharomyces pombe* or *Saccharomyces uvarum*. The transformation of yeast cells may for instance be effected by protoplast formation followed by transformation in a manner known per se.

Examples of suitable mammalian cell lines are the COS (ATCC CRL 1650), BHK (ATCC CRL 1632, ATCC CCL 10) or CHO (ATCC CCL 61) cell lines. Methods of transfecting mammalian cells and expressing DNA sequences introduced in the cells are described in e.g. Kaufman and Sharp, *J. Mol. Biol.* 159, 1982, pp. 601–621; Southern and Berg, *J. Mol. Appl. Genet.* 1, 1982, pp. 327–341; Loyter et al., *Proc. Natl. Acad. Sci. USA* 79, 1982, pp. 422–426; Wigler et al., *Cell* 14, 1978, p. 725; Corsaro and Pearson, *Somatic Cell Genetics* 7, 1981, p. 603, Graham and van der Eb, *Virology* 52, 1973, p. 456; and Neumann et al., *EMBO J.* 1, 1982, pp. 841–845.

Alternatively, fungal cells may be used as host cells. Examples of suitable fungal cells are cells of filamentous fungi, e.g. Aspergillus spp. or Neurospora spp., in particular strains of *Aspergillus oryzae* or *Aspergillus niger*. The use of Aspergillus spp. for the expression of proteins is described in, e.g., EP 238 023.

According to the present method, yeast cells are currently preferred for producing HSP and other SPs (such as those shown in FIG. 1), as they have surprisingly been found to produce SP in a high yield and in at least 60% glycosylated form. For instance, about two thirds of the HSP produced by yeast may be recovered in glycosylated form.

The medium used to cultivate the cells may be any conventional medium suitable for growing mammalian cells or fungal (including yeast) cells, depending on the choice of host cell. The spasmolytic polypeptide will be secreted by the host cells to the growth medium and may be recovered therefrom by conventional procedures including separating the cells from the medium by centrifugation or filtration, precipitating the proteinaceous components of the supernatant or filtrate by means of a salt, e.g. ammonium sulfate, purification by a variety of chromatographic procedures, e.g. ion exchange chromatography or affinity chromatography, or the like.

The present invention also relates to a pharmaceutical composition comprising HSP or a variant spasmolytic polypeptide of the invention together with a pharmaceutically acceptable carrier or excipient. In the composition of the invention, the variant may be formulated by any of the established methods of formulating pharmaceutical compositions, e.g. as described in Remington's Pharmaceutical Sciences, 1985. The composition may typically be in a form suited for oral or rectal administration and may, as such, be formulated as tablets or suppositories.

HSP or an SP variant of the invention is contemplated to be useful for the prophylaxis or treatment of gastrointestinal disorders. More specifically, it is contemplated for the treatment of gastric or peptic ulcers, inflammatory bowel disease, Crohn's disease or injury to the intestinal tract caused by radiation therapy, bacterial or other infections, etc.

EXAMPLE
MATERIAL AND METHODS
General methods

Standard DNA techniques were used as previously described [29]. Synthetic oligonucleotides were prepared on an automatic DNA synthesizer (380B, Applied Biosystems) using commercially available reagents. DNA sequence determinations were performed by the dideoxy chain-termination technique [30]. Polymerase chain reactions (PCR) were performed on a DNA Thermal Cycler (Perkin Elmer Cetus) using a commercial kit (GeneAmp, Perkin Elmer Cetus).

PCR cloning of HSP

The first trefoil domain of HSP was isolated by a PCR reaction in which 1 µg human genomic DNA (Clontech, Palo Alto, Calif., U.S.A.) was used as a template. The reaction mixture contained 100 pmole each of the forward primer 1 (GGCTGAGCCCCCATAACAG) (SEQ ID NO:4) and reverse primer 2 (TGGAAACACCAGGGGAC) (SEQ ID NO:5) (FIG. 3) and was carried out in a 100 µl volume. The cycle was :94° C. for 1 min, 50° C. for 1 min, and 72° C. for 1 min. After 30 cycles a final cycle was performed in which the 72° C. step was maintained for 10 min. The PCR product, a 115 bp fragment, was isolated by electrophoresis on a 2% agarose gel.

The 115 bp PCR fragment was digested with DdeI and then ligated to a 31 bp duplex formed from the oligonucleotides (GAGAAACCCTCCCCCTGCCAGTGCTCCAGGC) (SEQ ID NO:6) and (TCAGCCTGGAGCACTGGCAGGGGGAGGGTTTCTC) (SEQ ID NO:7). The ligation product was amplified by PCR using forward primer 3 (GCTGAGAGATTGGAGA-AGAGAGAGAAACCCTCCCCCT) (SEQ ID NO:8) and reverse primer 2. The 3' part of primer 3 is identical to the N-terminal encoding part of the HSP gene and the 5' part of primer 3 is identical to the C-terminal encoding part of the hybrid leader gene (FIG. 3). In-frame fusion of the hybrid leader gene and the first trefoil domain from HSP was obtained by overlay extension PCR [31]. The product was digested with EcoRI and AvaII and isolated as a 360 bp DNA fragment.

The second trefoil domain of HSP was PCR-cloned from human genomic DNA as described for the first domain by replacing primers 1 and 2 with forward primer 4 (TGCGTCATGGAGGTCTC) (SEQ ID NO:9) and reverse primer 5 (AGCACCATGGCACTTCAAAG) (SEQ ID NO:10) (FIG. 3). Reverse primer 5 introduces a NcoI site as a silent mutation. The PCR product, a 115 bp fragment, was isolated and digested with DdeI and NcoI resulting in a 91 bp fragment. To this fragment were ligated two synthetic duplexes. The first, encoding the amino acid sequence between the two trefoil domains, consisted of the oligonucleotides (GTCCCCTGGTGTTTCCACCCCCTCCC-AAAGCAAGAGTCGGATCAGTGCGTCATGGAGGTC) (SEQ ID NO:11) and (TGAGACCTCCATGACG-CACTGATCCGACTCTTGCTTTGGAGGGGTGGAAA-CACCAGGG) (SEQ ID NO:12). The second, a 46 bp NcoI—XbaI fragment encoding the C-terminal part of HSP, consisted of the oligonucleotides (CATGGTGCTTCT-TCCCGAACTCTGTGGAAGACTGCCATTACTAAGT) (SEQ ID NO:13) and (CTAGACTTAGTAATG-GCAGTCTTCCACAGAGTTCGGGAAGAAGCAC) (SEQ ID NO:14). After AvaII digestion a 195 bp AvaII—XbaI fragment was isolated.

A DNA construct encoding the hybrid leader fused in-frame to the entire HSP gene was obtained by ligation of the 360 bp EcoRI—AvaII fragment and the 195 bp AvaII—XbaI fragment described above to the 2.7 kb EcoRI—XbaI fragment from vector pTZ19R [32]. This construct was then transformed into E. coli strain MT-172 (r⁻, m⁺) by selection for resistance to ampicillin. DNA sequencing of the resulting plasmid, KFN-1843, showed that the correct construction had been obtained.

Construction of the HSP secreting yeast strain

Figure 4:
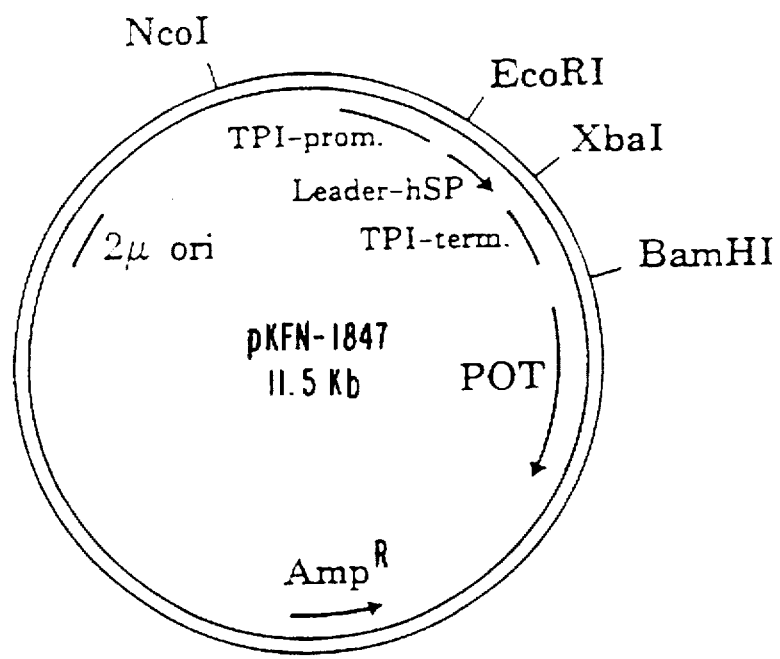
FIG. 4 shows the *S. cerevisiae* plasmid for the expression and secretion of HSP. TPI-prom. and TPI-term. are *S. cerevisiae* triosephosphate isomerase transcription promoter and terminator sequences, respectively. POT is a selective marker, the *Schizosaccharomyces pombe* triosephosphate isomerase gene. Only restriction sites relevant for the construction of the plasmid have been indicated.

Plasmid KFN-1843 described above was digested with EcoRI and XbaI. The resulting 558 bp fragment was isolated and ligated to the 9.3 kb NcoI—XbaI fragment and the 1.6 kb NcoI—EcoRI fragment both from the yeast expression vector pMT-636. Plasmid pMT-636 is derived from the S. cerevisiae—E. coli shuttle vector CPOT [25,33] by deletion of the 0.4 kb HpaI—NruI fragment from the Leu-2 gene. The ligation mixture was transformed into E. coli strain MT-172, and the HSP expression plasmid, KFN-1847, was isolated (FIG. 4). Plasmid pKFN-1847 was transformed into S. cerevisiae strain MT-663 by selection for growth on glucose as the sole carbon source. One transformant, KFN-1852, was selected for fermentation.

Fermentation

The transformant described above was cultivated at 30° C. for 3 days in yeast peptone dextrose (YPD) medium [40] supplied with additional yeast extract (60 g/l). An OD 650 nm value of 52 was reached at the end of the fermentation.

Purification of r-HSP

Figure 5:
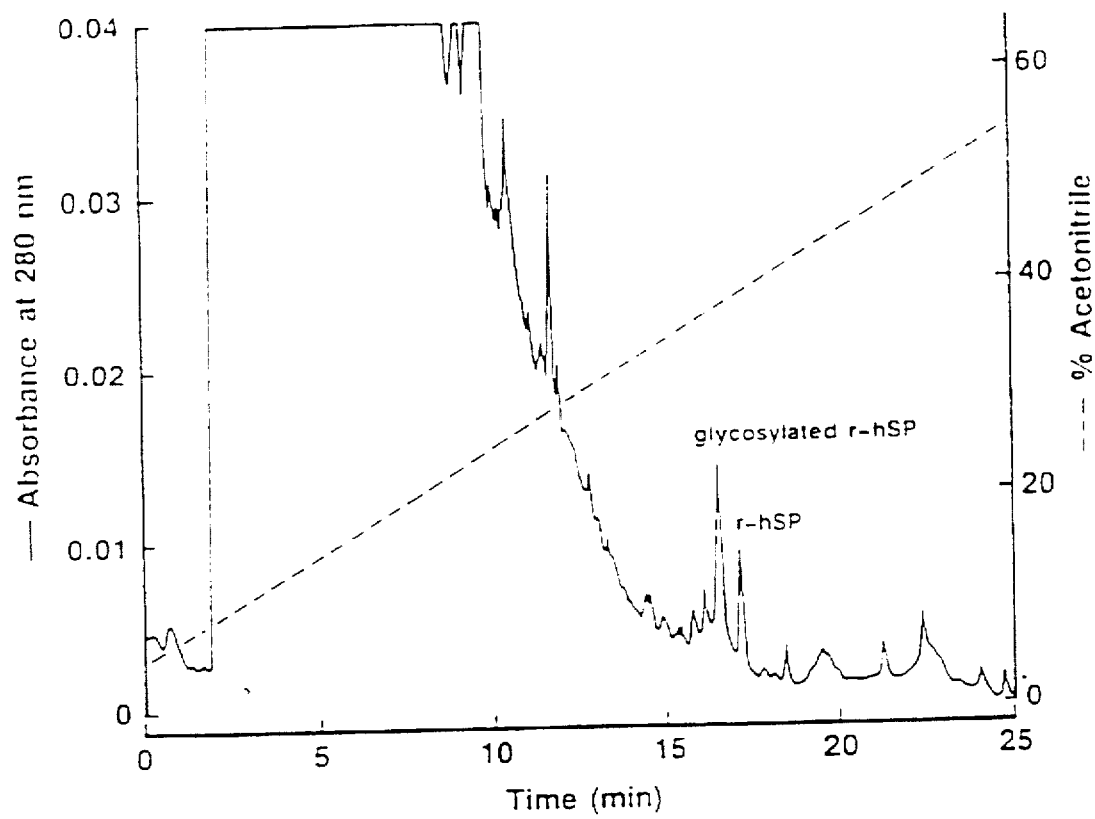
FIG. 5 shows reversed-phase HPLC on a Vydac 214TP54 column of yeast fermentation broth. The two peaks corresponding to r-HSP and glycosylated r-HSP are indicated. The dashed line shows the concentration of acetonitrile in the eluting solvent.

The concentration of r-HSP in the yeast fermentation broth and fractions obtained during the purification was measured by analytical HPLC. Aliquots (usually 50–200 µl) were injected onto a Vydac 214TP54 reverse-phase C4 HPLC column (0.46×25 cm) equilibrated at 30° C. at a flow rate of 1.5 ml/min with 0.1% (v/v) TFA in 5% (v/v) acetonitrile. The concentration of acetonitrile in the eluting solvent was raised to 65% (v/v) over 30 min. Absorbance was measured at 280 nm. The peaks eluting at 15.6 min. and 16.1 min. (FIG. 5) was found by mass spectrometry analysis to represent glycosylated r-HSP and unglycosylated r-HSP.

respectively. The peptides were quantified using a calibrated PSP sample as standard as both peptides contain two Trp and two Tyr out of 106 amino acid residues.

From a 10 litre fermentor, 8 litres of fermentation broth was isolated by centrifugation at 3,000 rpm for 10 min. The supernatant was concentrated to 0.9 litre using an Amicon ultrafiltration unit (RA 2000) equipped with an Amicon spiral ultrafiltration cartridge type S1Y3, MW cutoff 3,000 (Product No. 540620). The pH was adjusted to 1.7 and the conductivity in the resulting concentrated sample was measured to 4.7 mS.

Figure 6:
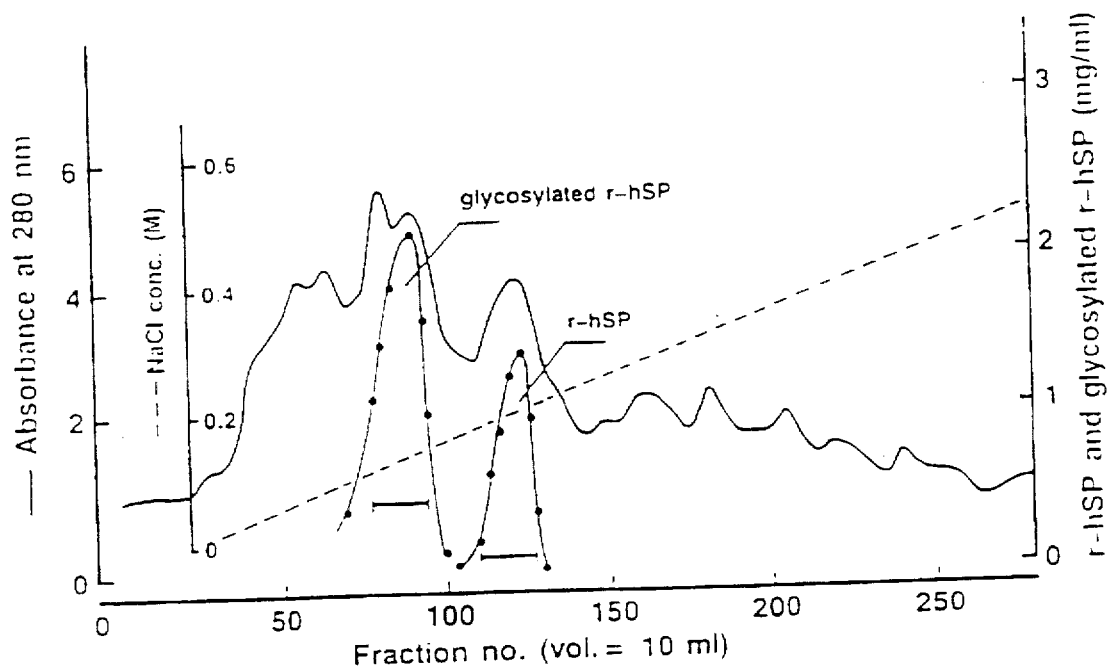
FIG. 6 shows ion exchange chromatography on a Fast Flow S column of concentrated yeast supernatant. The amount of r-HSP and glycosylated r-HSP were determined by the use of the HPLC system shown in FIG. 5. The bars indicate the fractions pooled for further purification of r-HSP and glycosylated r-HSP. The dashed line shows the concentration of NaCl in the eluting solvent. For details, see Material and Methods.

The sample was pumped onto a Fast Flow S-Sepharose (Pharmacia) column (5×11 cm) with a flow rate of 40 ml/h. Previous to the application, the column was equilibrated in 50 mM formic acid buffer, pH=3.7. After application of the sample, the column was washed with 500 ml of 50 mM formic acid buffer, pH=3.7. The peptides were eluted from the column by a linear gradient between 1.5 litres of 50 mM formic acid buffer, pH=3.7 and 1.5 litres of 50 mM formic acid buffer, pH=3.7 containing 0.6M NaCl. Fractions of 10 ml was collected at a flow rate of 40 ml/h and the absorbance was measured at 280 nm. Fractions were assayed for the content of r-HSP and glycosylated r-HSP in the HPLC-system previously described. The elution profile is shown in FIG. 6. Fractions corresponding to r-HSP (fract. Nos. 107–128) and glycosylated r-HSP (fract. Nos. 78–95), respectively, were pooled.

Figure 7A:
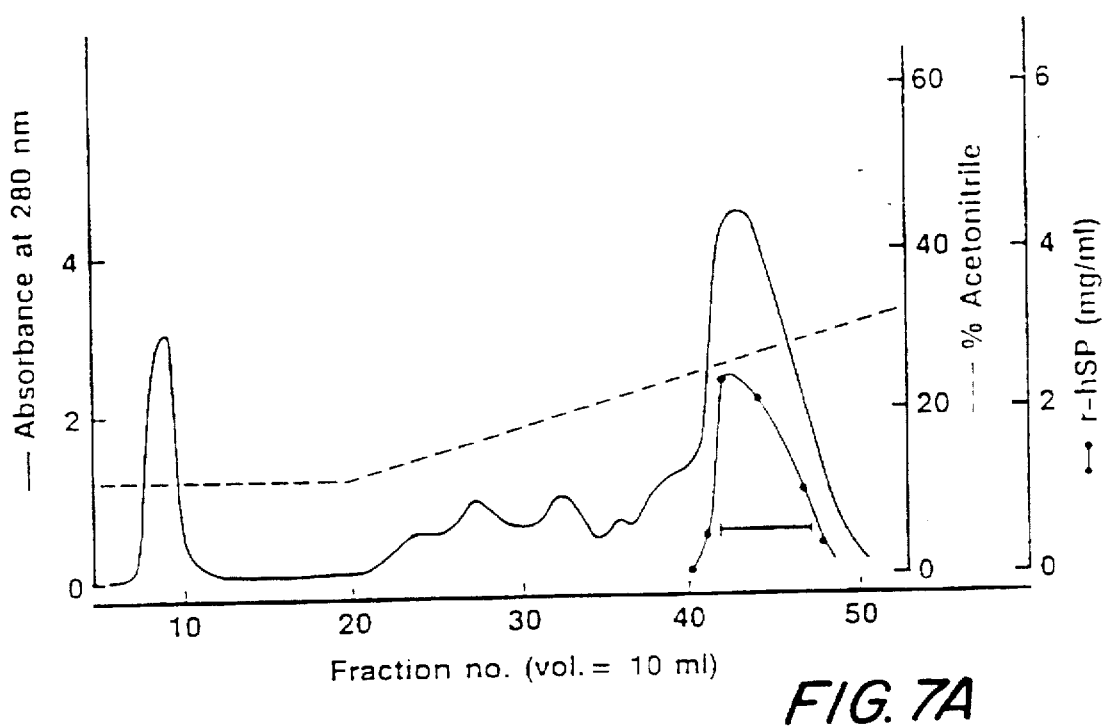
FIG. 7 shows the final purification of r-HSP (A) and glycosylated r-HSP (B) on a preparative reversed-phase HPLC Vydac 214TP1022 column. The bars indicate the fractions pooled for lyophilization. The dashed lines show the concentration of acetonitrile in the eluting solvent. For details, see Material and Methods.
Figure 7B:
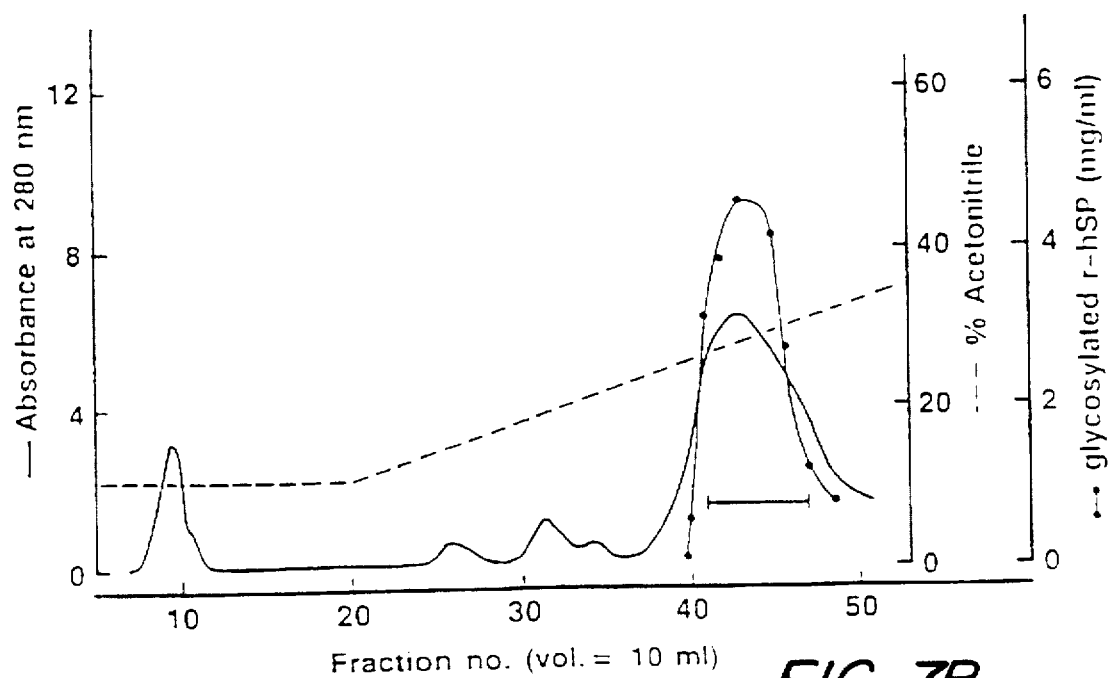

Glycosylated r-HSP and r-HSP were further purified by preparative HPLC chromatography. Pooled fractions (approx. 200 ml) were pumped onto a Vydac 214TP1022 C4 column (2.2×25 cm) equilibrated in 0.1% (v/v) TFA. The column was washed with 100 ml of 0.1% (v/v) TFA in 10% (v/v) MeCN. The peptides were eluted at 25° C. and at a flow rate of 5 ml/min with a linear gradient (650 ml) formed from MeCN/$H_2$O/TFA (10.0:89.9:0.1 v/v/v) and MeCN/$H_2$O/TFA (60.0:39.9:0.1 v/v/v). UV-absorption was monitored at 280 nm, and fractions corresponding to 10 ml were collected and analysed for the content of r-HSP or glycosylated r-HSP. FIG. 7 shows the preparative HPLC purification of r-HSP (FIG. 7A) and glycosylated r-HSP (FIG. 7B). Fractions correspomding to the bars were pooled, and the volume reduced to 30% by vacuum centrifugation. From the two resulting pools, r-HSP and glycosylated r-HSP were isolated by lyophilization.

Characterization of r-HSP and glycosylated r-HSP

Amino acid composition analysis were carried out by hydrolysis of 50 µg peptide with 6M HCl for 24 h at 110° C. as previously described [6]; no correction for loss during hydrolysis was carried out. Amino acid sequence analysis was determined by automated Edman degradation using an Applied Biosystems Model 470A gas-phase sequencer [22]. Carbohydrate composition analysis was carried out by hydrolysis of 50 µg peptide with 2M HCl for 1 h, 2 h and 4 h at 100° C. and monosaccharides were separated on a CarboPac PAI (Dionex, Sunnyvale, Calif.) column (4×250 mm) eluted with 14 mM NaOH. The monosaccharides were detected by pulsed amperometric detection (Dionex PAD-detector). The amount of monosaccharides was corrected to zero time of hydrolysis and calculated as nmol of monosaccharide per nmol of peptide.

Mass spectrometry analysis was performed using an API III LC/MS/MS system (Sciex, Thornhill, Ontario, Canada). The triple quadrupole instrument has a mass-to-charge (m/z) range of 2400 and is fitted with a pneumatically assisted electrospray (also referred to as ion-spray) interface [23,24]. Sample introduction was done by a syringe infusion pump (Sage Instruments, Cambridge, Ma.) through a fused capillary (75 µm i.d.) with a liquid flow-rate set at 0.5–1 µl/min. The instrument m/z scale was calibrated with the singly-charged ammonium adduct ions of poly(propylene glycols) (PPG's) under unit resolution.

The accuracy of mass measurements was generally better than 0.02%.

RESULTS

Expression and purification

DNA fragments encoding the two trefoil domains of HSP were isolated by PCR from human genomic DNA using primers based on the published CDNA sequence [8]. The full length HSP gene was obtained from the PCR cloned fragments by addition of synthetic DNA fragments. The HSP gene was fused in-frame to a hybrid yeast leader sequence by overlay extension PCR [31] (FIG. 3). The hybrid leader is based on the mouse salivary amylase signal peptide [34] and the *S. kluyveri* α mating factor leader sequence [35] and is further modified near the Kex 2 cleavage site for efficient processing [36, 41].

The yeast expression plasmid pKFN-1847 contains the leader-HSP gene inserted between the *S. cerevisiae* triose phosphate isomerase promoter and terminator [37]. The expression vector (FIG. 4) also contains the *Schizosaccharomyces pombe* TPI gene (POT) [38].

The plasmid was transformed into the yeast strain MT-663, carrying a deletion in the TPI gene, by selecting for growth on glucose.

The expression level of r-HSP in the present yeast system is approx. 120 mg/l. As can be seen from FIG. 5, the yeast supernatant contains two forms of r-HSP; one eluting at $R_t$=15.6 min. and one eluting at $R_t$=16.1 min. These two forms were purified separately, and by using the analytical HPLC-system (FIG. 5), these two forms can be quantified individually during the different steps of the purification.

After the initial concentration of the yeast supernatant by ultrafiltration, the first purification step was cationic exchange chromatography on a Fast Flow S column. FIG. 6 shows the elution profile from the column including the amount of r-HSP and glycosylated r-HSP determined in the fractions. A complete separation of the two forms of r-HSP was obtained in this step.

The fractions from the Fast Flows S column were pooled as indicated in FIG. 6, and the two peptides were further purified by preparative HPLC (FIG. 7). The r-HSP and glycosylated r-HSP were recovered from the fractions indicated in FIG. 7A and FIG. 7B by vacuum centrifugation and lyophilization. The purification is summarized in Table 1. The overall yield of r-HSP and glycosylated r-HSP from 8 litres of fermentation broth was 160 mg and 219 mg corresponding to 50% and 34%, respectively.

Characterization of r-HSP and glycosylated r-HSP

Figure 8A:
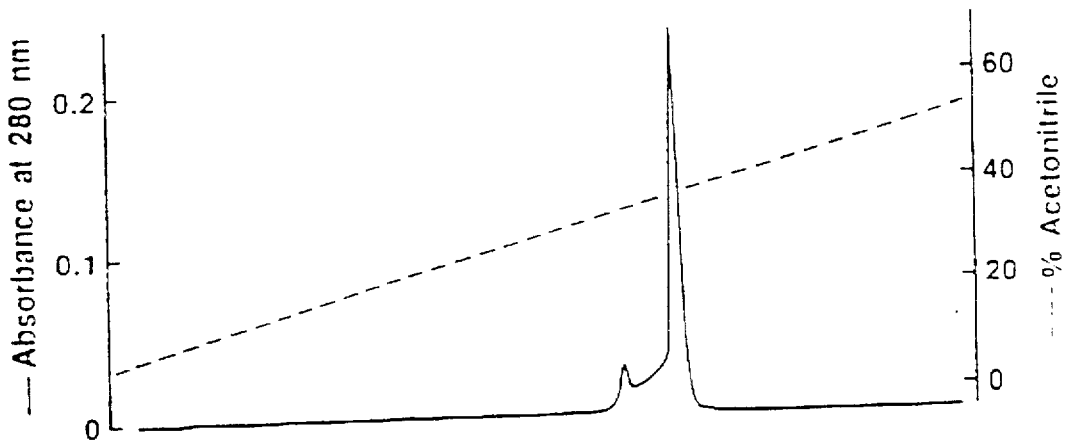
FIG. 8 shows reversed-phase HPLC on a Vydac 214TP54 column of purified, glycosylated r-HSP (A) and r-HSP (B). The dashed lines show the concentration of acetonitrile in the eluting solvent.
Figure 8B:
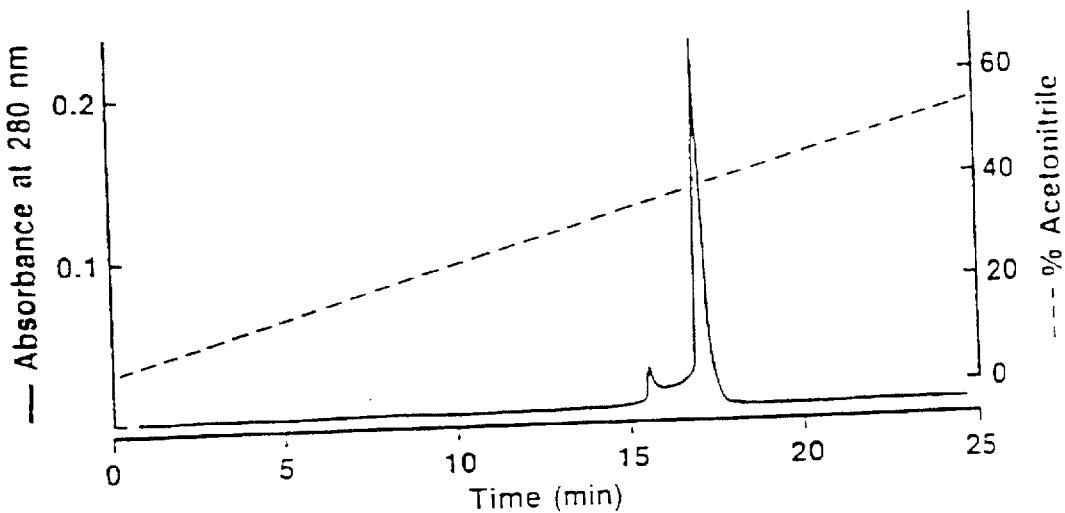
Figure 9A:
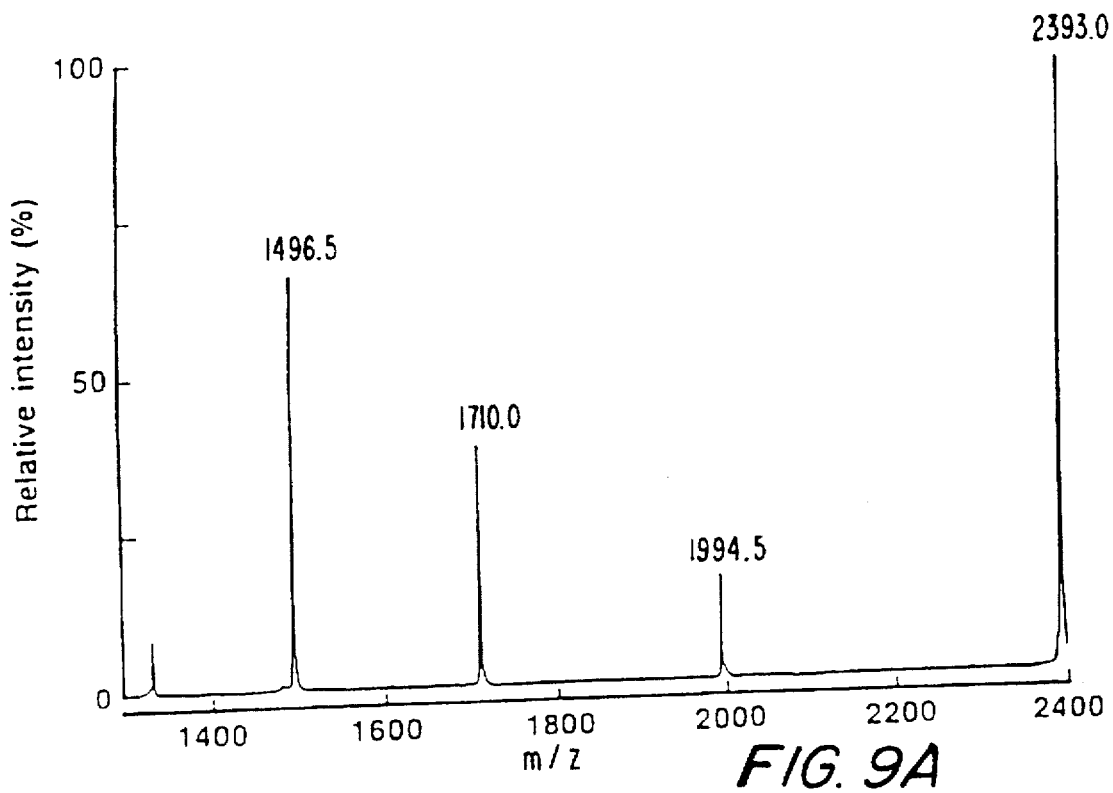
FIG. 9 shows mass spectra of purified r-HSP (A and B) and glycosylated r-HSP (C and D). FIG. A and FIG. C show the original mass spectrum of r-HSP and glycosylated r-HSP, respectively. FIG. B and FIG. D show the reconstructed mass spectrum for r-HSP and glycosylated r-HSP on the basis of FIG. A and FIG. C.
Figure 9B:
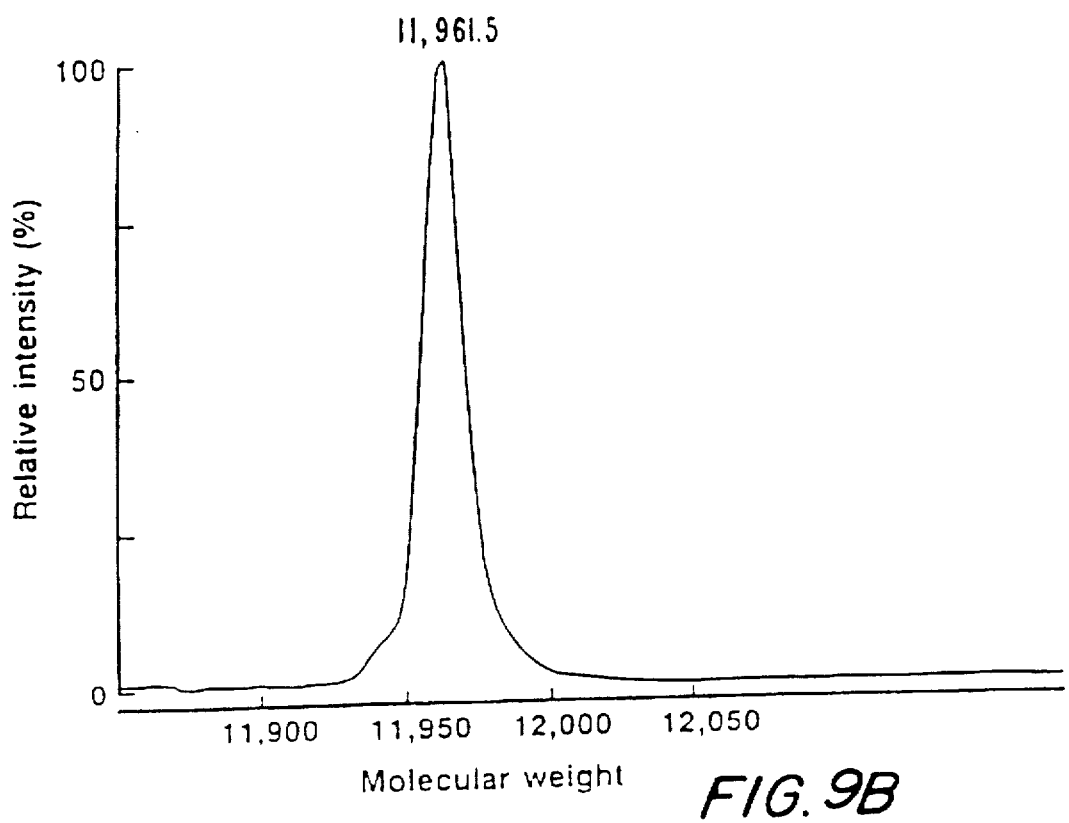
Figure 9C:
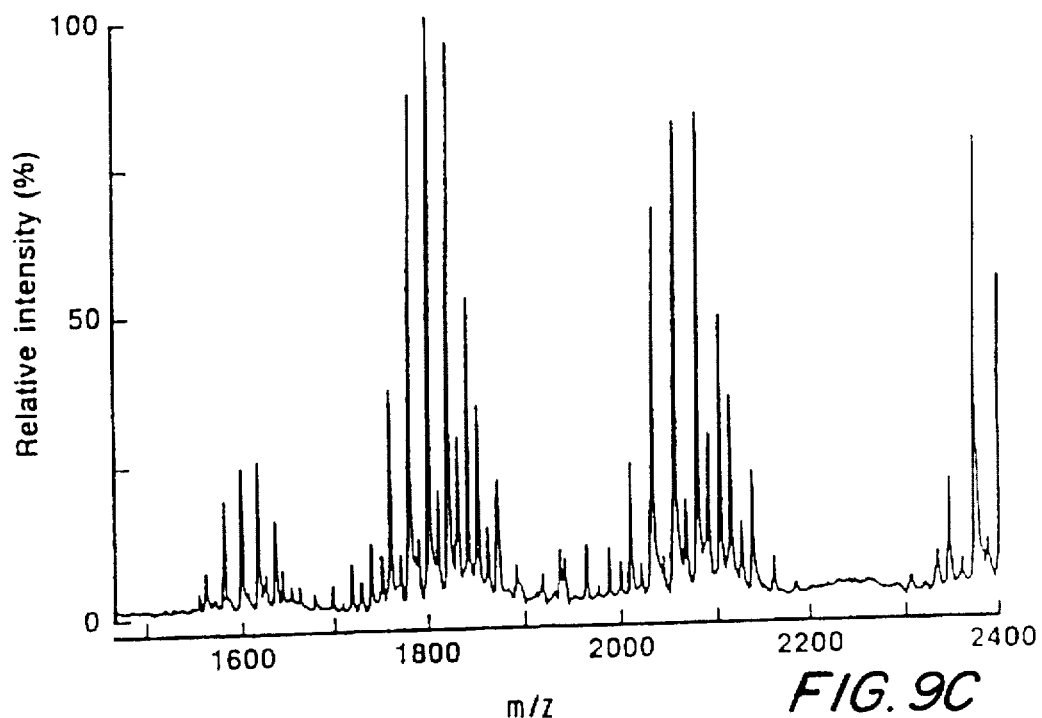
Figure 9D:
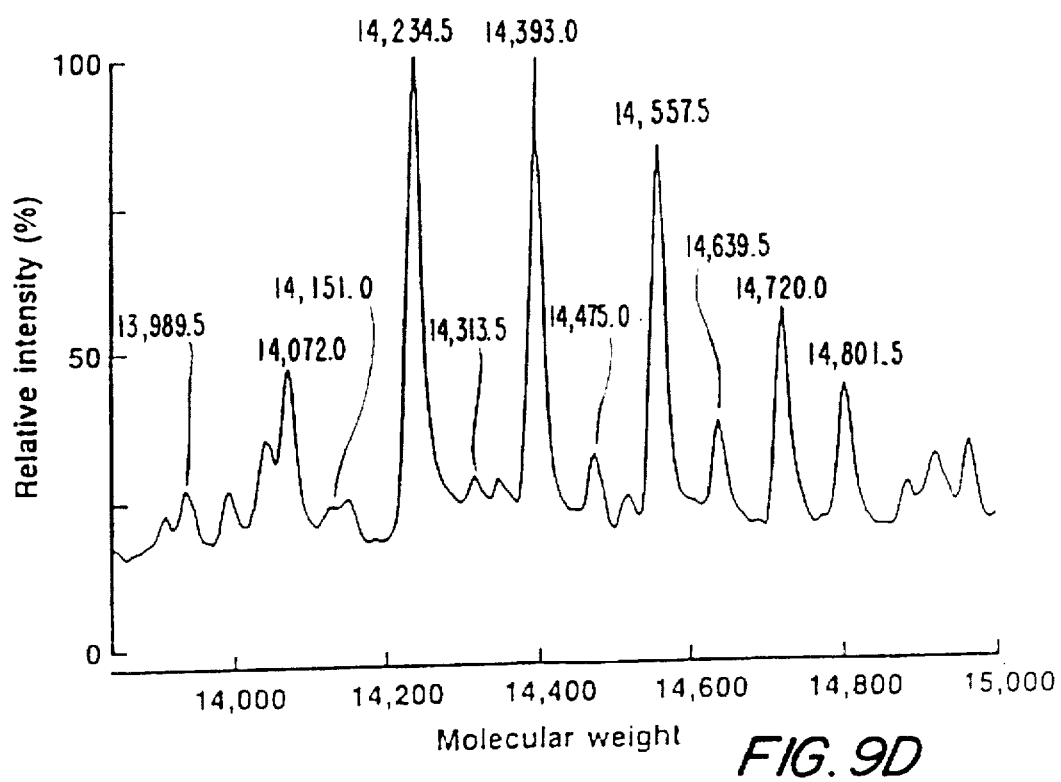

FIG. 8 shows the purity of r-HSP and glycosylated r-HSP as analysed by analytical HPLC. From these results none of the peptides looks completely pure. However, upon rechromatography of material eluting in the minor as well as the major peak, similar chromatograms were obtained for both peptides (results not shown). This seems to indicate that the double peak observed for both r-HSP and glycosylated r-HSP reflects an atypical behaviour of these peptides on reverse phase columns rather than impurities in the preparations.

Table 2 shows the amino acid sequencing results obtained on r-HSP and glycosylated r-HSP. The average repetitive yield was 94.4% (r-HSP) and 94.6% (glycosylated r-HSP), respectively. In both cases the first 40 residues of the two peptides were confirmed by the sequence analysis. In the glycosylated HSP, no PTH-a.a. was found in Edman degradation cycle No. 15. The HSP sequence from residue 15–17 (Asn-Arg-Thr) corresponds to a consensus sequence for N-glycosylation of Asn-15.

The carbohydrate composition analysis of glysocylated r-HSP showed the presence of 12.8 nmol mannose (Man) and 1.6 nmol of N-acetyl glucoseamine (GlcNAc) per nmol of r-HSP. By peptide mapping of r-HSP and glycosylated r-HSP in combination with mass spectrometry and sequencing analysis (results not shown), no other residue besides Asn-15 of the glycosylated r-HSP was found to be modified, i.e. no O-glycosylation was found.

In FIG. 9, the electro-spray mass spectrometry (ESMS) analysis is shown for r-HSP and glycosylated r-HSP. FIG. 9A and 9C are original mass spectra displaying characteristics series of multiply charged protonated ions always observed in ESMS spectra of proteins. FIG. 9B and 9D are the corresponding computer reconstructed mass spectra from which the molecular weight of individual components may be read directly. As can be seen from FIG. 9B, the MW found for r-HSP is 11961.5±2 which is in very good agreement with a calculated mass of 11961.3. FIG. 9D shows the reconstructed ion spray mass spectrum of the glycosylated r-HSP. From the sequence analysis and the carbohydrate composition analysis, it is known that only Asn-15 is glycosylated and that only two monosaccharide residues, mannose and N-acetyl glucoseamine, occur in the glycosylated form of r-HSP. From these results in combination with the mass spectrometry data, it is possible glycosyduce the different glycosylated forms of r-HSP (Table 3).

Molecular weights corresponding to two series of carbohydrate side chains can be deduced from the combination of carbohydrate composition data and ISMS-data, namely $(GlcNAc)_2(Hex)_{1-15}$ and $(Hex)_{13-17}$ (Table 3). As mannose is the only hexose in the glycosylated r-HSP, and as Asn-15 is the only glycosylated residue, it seems reasonable to conclude that the structure of the glycosylation site is Asn-$(GlcNAc)_2$-$(Man)_{10-15}$. The observed Asn-$(Hex)_{13-17}$ forms are thus most likely to arise from fragmentation in the mass spectrometer, by which the two GlcNAc residues lose an acetyl group and are converted into two hexoses.

The structure of Asn-$(GlcNAc)_2$-$(Man)_{10-15}$ has previously been reported as high mannose type of N-glycosylation for other peptides and proteins expressed in yeast [26].

TABLE 1

Purification of r-hSP and glycosylated r-hSP from yeast supernatant

| STEP | | Volume [ml] | Amount [mg] r-hSP | Amount [mg] glycosylated r-hSP | Yield [%] r-hSP | Yield [%] glycosylated r-hSP |
|---|---|---|---|---|---|---|
| Yeast supernatant | | 8000 | 320 | 640 | 100 | 100 |
| Ultrafiltration | | 900 | 207 | 405 | 65 | 63 |
| Ion exchange | Pool 1 | 160 | | 275 | | 43 |
| chromatography | Pool 2 | 220 | 182 | | 57 | |
| Prep HPLC | Pool 1 | 54 | | 219 | | 34 |
| | Pool 2 | 80 | 160 | | 50 | |

TABLE 2

Amino acid sequence analysis of r-hSP and glycosylated r-hSP

| | | Yield (pmol) | |
|---|---|---|---|
| Cycle No. | PTH-a.a | r-hSP | glycosylated r-hSP |
| 1 | Glu | 4304 | 8853 |
| 2 | Lys | 6925 | 8292 |
| 3 | Pro | 6027 | 12837 |
| 4 | Ser | 2890 | 5602 |
| 5 | Pro | 4336 | 8802 |
| 6 | (Cys) | ND | ND |
| 7 | Gln | 3388 | 5689 |
| 8 | (Cys) | ND | ND |
| 9 | Ser | 1279 | 2417 |
| 10 | Arg | 1876 | 2523 |
| 11 | Leu | 2277 | 4290 |
| 12 | Ser | 877 | 1790 |
| 13 | Pro | 1545 | 2963 |
| 14 | His | 517 | 574 |
| 15 | Asn | 1202 | 0* |
| 16 | Arg | 959 | 1471 |
| 17 | Thr | 978 | 2172 |
| 18 | Asn | 1066 | 1509 |
| 19 | (Cys) | ND | ND |
| 20 | Gly | 836 | 1857 |
| 21 | Phe | 993 | 1958 |
| 22 | Pro | 843 | 1839 |
| 23 | Gly | 785 | 2049 |
| 24 | Ile | 640 | 1400 |
| 25 | Thr | 589 | 1454 |
| 26 | Ser | 274 | 621 |
| 27 | Asp | 581 | 1391 |
| 28 | Gln | 445 | 952 |
| 29 | (Cys) | ND | ND |
| 30 | Phe | 623 | 1562 |
| 31 | Asp | 483 | 1210 |
| 32 | Asn | 369 | 823 |
| 33 | Gly | 359 | 885 |
| 34 | (Cys) | ND | ND |
| 35 | (Cys) | ND | ND |
| 36 | Phe | 422 | 1094 |
| 37 | Asp | 268 | 783 |
| 38 | Ser | 127 | 324 |
| 39 | Ser | 145 | 394 |
| 40 | Val | 298 | 827 |

ND: Not determined
*: No trace of PTH-Asn or PTH-Asp was seen in cycle No. 15 of glycosylated r-hSP.

TABLE 3

Mass analysis of glycosylated r-hSP

| Structure | Calculated MW | MW found by ESMS (FIG. 9D) |
|---|---|---|
| hSP + 2 GlcNAc + 10 Man | 13989.1 | 13989.5 |
| hSP + 2 GlcNAc + 11 Man | 14151.2 | 14151.0 |
| hSP + 2 GlcNAc + 12 Man | 14313.4 | 14313.5 |
| hSP + 2 GlcNAc + 13 Man | 14475.5 | 14475.0 |
| hSP + 2 GlcNAc + 14 Man | 14639.7 | 14639.5 |
| hSP + 2 GlcNAc + 15 Man | 14799.8 | 14801.5 |
| hSP + 13 Man | 14069.1 | 14072.0 |
| hSP + 14 Man | 14231.3 | 14232.5 |
| hSP + 15 Man | 14393.4 | 14393.0 |
| hSP + 16 Man | 14555.5 | 14557.5 |
| hSP + 17 Man | 14717.7 | 14720.0 |

REFERENCES

[1] Thim, L. (1989) FEBS Lett. 250, 85–90.
[2] Suemori, S., Lynch-Devaney, K. and Podolsky, D. K. (1991) Proc. Natl. Acad. Sci. U.S.A. 88, 11017–11021.

[3] Jakowlew, S. B., Breathnach, R., Jeltsch, J. M., Masiakowski, P. and Chambon, P. (1984) Nucleic Acids Res. 12, 1861–2878.

[4] Prud'homme, J.-F., Fridlansky, F., Le Cunff, M., Atger, M., Mercier-Bodart, C., Pichon, M.-F. and Milgrom, E. (1985) DNA 4, 11–21.

[5] Rio, M. C., Bellocq, J. P., Daniel, J. Y., Tomasetto, C., Lathe, R., Chenard, M. P., Batzenschlager, A. and Chambon, P. (1988) Science 241, 705–708.

[6] Thim, L., Thomsen, J., Christensen, M. and Jørgensen, K. H. (1985) Biochim. Biophys. Acta 827, 410–418.

[7] Rose, K., Savoy, L.-A., Thim, L., Christensen, M. and Jørgensen, K. H. (1989) Biochim. Biophys. Acta 998, 297–300.

[8] Tomasetto, C., Rio, M.-C., Gautier, C., Wolf, C., Hareuveni, M., Chambon, P. and Lathe, R. (1990) EMBO J. 9, 407–414.

[9] Hoffmann, W. (1988) J. Biol. Chem. 263, 7686–7690.

[10] Hauser, F. and Hoffmann, W. (1991) J. Biol. Chem. 266, 21306–21309.

[11] Hauser, F., Roeben, C. and Hoffmann, W. (1992) J. Biol. Chem. 267, 14451–14455.

[12] Jørgensen, K. H., Thim, L. and Jacobsen, H. E. (1982) Regul. Peptides 3, 207–219.

[13] Thim, L., Jørgensen, K. H. and Jørgensen, K. D. (1982) Regul. Peptides 3, 221–230.

[14] Rasmussen, T. N., Raabjerg, L., Poulsen, S. S., Thim, L. and Holst, J. J. (1992) Histochemistry 98, 113–119.

[15] Frandsen, E. K., Jørgensen, K. H. and Thim, L. (1986) Regul. Peptides 16, 291–297.

[16] Frandsen, E. K. (1988) Regul. Peptides 20, 45–52.

[17] Rasmussen, T. N., Raabjerg, L., Poulsen, S. S., Thim, L. and Holst, J. J. (1992) Am. J. Physiol. (in press)

[18] Jørgensen, KD., Diamant, B., Jørgensen, K. H. and Thim, L. (1982) Regul. Peptides 3, 231–243.

[19] Hoosein, N. M., Thim, L., Jørgensen, K. H. and Brattain, M. G. (1989) FEBS Lett. 247, 303–306.

[20] Wright, N. A., Poulsom, R., Stamp, G. W., Hall, P. A., Jeffery, R. E., Longcroft, J. M., Rio, M.-C., Tomasetto, C. and Chambon, P. (1990) J. Pathol. 162, 279–284.

[21] Rio, M.-C., Chenard, M.-P., Wolf, C., Marcellin, L., Tomasetto, C., Lathe, R., Bellocq, J. P. and Chambon, P. (1991) Gastroenterology 100, 375–379.

[22] Thim, L., Hansen, M. T. and Soerensen, A. R. (1987) FEBS Lett. 212, 307–312.

[23] Bruins, A. P., Covey, T. R. and Henion, J. D. (1987) Anal. Chem. 59, 2642–2646.

[24] Covey, T. R., Bonner, R. F., Shushan, B. I. and Henion, J. D. (1988) Rapid Commun. Mass Spectrom. 2, 249–256.

[25] Thim, L., Hansen, M. T., Norris, K., Hoegh, I., Boel, E., Forstrom, J., Ammerer, G. and Fiil, N. P. (1986) Proc. Natl. Acad. Sci. U.S.A. 83, 6766–6770.

[26] Poulter, L. and Burlingame, A. L. (1990) in: Methods in Enzymology (McCloskey, J. A., ed.) 193, 661–689. Academic Press, Inc., San Diego, Calif.

[27] Gajhede, M., Thim, L., Jørgensen, K. H. and Melberg, S. G. (1992) Proteins: Structure, Function, and Genetics 13, 364–368.

[28] Carr, M. D. (1992) Biochemistry 31, 1998–2004.

[29] Sambrook, J., Fritch, E. F., and Maniatis, T. (1989) Molecular Cloning: A Laboratory Manual, Second Edition, Cold Spring Harbor Laboratory Press, Cold Spring Harbor, N.Y.

[30] Sanger, F., Micklen, S., and Coulson, A. R. (1977) Proc. Natl. Acad. Sci. U.S.A. 74, 5463–5467.

[31] Horton, R. M., Hunt, H. D., Ho, S. N., Pullen, J. K., and Pease, L. R. (1989) Gene 77, 61–68.

[32] Mead, D. A., Szczesna-Skorupa, E. and Kemper, B. (1986) Prot. Engin. 1, 67–74.

[33] Kawasaki, G. (1984) 12th International Conference on Yeast Genetics and Molecular Biology, Sep. 17–24, 1984, Edinburgh, Scotland, Abstr. P15.

[34] Hagenbuchle, O., Tosi, M., Schibler, U., Bovey, R., Wellauer, P. K., and Young, R. A. (1981) Nature 289, 643–646.

[35] Egel-Mitani, M. and Hansen, M. T. (1987) Nucl. Acids Res. 15, 6303–6304.

[36] Christiansen, L. and Norris, K., personal communication.

[37] Alber, T. and Kawasaki, G. (1982) J. Mol. Appl. Genet. 1, 419–434.

[38] Russell, P. R. (1985) Gene 40, 125–130.

[39] Jeltsch, J. M., Roberts, M., Schatz, C., Garnier, J. M., Brown, A. M. C., and Chambon, P. (1987) Nucl. Acids. Res. 15, 1401–1414.

[40] Sherman, F., Fink, G. R. and Hicks, J. B. (1981) Methods in Yeast Genetics. Cold Spring Harbor Laboratory Press, New York.

[41] Norris, K., Norris, F. and Bjoern, S. E. (1990) International Patent Application WO 90/10075.

---

What is claimed is:

1. Human spasmolytic polypeptide (HSP) characterized by being in glycosylated form, and wherein glycosylation is at Asn15, and wherein said HSP has an amino acid sequence that differs from SEQ ID NO:1 by comprising one or more of the following substitutions: Lys2 replaced by Asn, Gln7 replaced by Asn, Arg10 replaced by Asn, Gly20 replaced by Thr or Ser, Gly23 replaced by Asn, Ile24 replaced by Asn, Phe36 replaced by Asn, Asp37 replaced by Asn, Ser39 replaced by Asn, Gln53 replaced by Asn, Glu61 replaced by Asn, Asp64 replaced by Asn, Arg66 replaced by Thr or Ser, Gly69 replaced by The or Ser, Gly72 replaced by Asn, Ile89 replaced by Thr or Ser, Pro98 replaced by Asn or Val101 replaced by Thr or Ser, and wherein said HSP has spasmolytic activity.

2. HSP according to claim 1, in which the glycosylated side chain contains at least one hexose unit.

3. HSP according to claim 2, in which the glycosylated side chain contains at least one mannose unit.

4. HSP according to claim 3, in which the glycosylated side chain contains 13–17 mannose units.

5. HSP according to claim 1, which in addition is glycosylated with at least one unit of N-acetyl glucosamine (GlcNAc).

6. HSP according to claim 1, which is glycosylated with $(GlcNAc)_2(Man)_{10-15}$.

7. HSP according to claim 1, wherein Asp64 is replaced by Asn, and Arg66 is replaced by Thr or Ser.

8. A pharmaceutical composition comprising HSP according to claim 1 together with a pharmaceutically acceptable carrier or excipient.

9. A method for the treatment of gastrointestinal disorders, comprising administering the pharmaceutical composition of claim 8.

10. A variant of a spasmolytic polypeptide which is a fragment of human spasmolytic polypeptide (HSP) having the amino acid sequence of SEQ ID NO:1 comprising at least one trefoil domain from position 8 to 46 or position 58 to 95, and wherein Asn15 is substituted by Asp or Glu, wherever said variant has spasmolytic activity.

11. A variant according to claim 10, wherein Thr17 is substituted by another amino acid except Ser, wherein said variant has spasmolytic activity.

12. A variant of the fragment of HSP according to claim 10, wherein Arg10 is replaced by Asn, Gly 20 is replaced by Thr or Ser, Gly23 is replaced by Asn, Ile 24 is replaced by Asn, Phe 36 is replaced by Asn, Asp 37 is replaced by Asn, Ser39 is replaced by Asn, Glu61 is replaced by Asn, Asp64 is replaced by Asn, Arg66 is replaced by Thr or Ser, Gly69 is replaced by Thr or Ser, or Gly72 is replaced by Asn, or a combination of two or more of these substitutions, wherein said variant has spasmolytic activity.

13. A pharmaceutical composition comprising a variant spasmolytic polypeptide according to claim 10 together with a pharmaceutically acceptable carrier or excipient.

14. A method for the treatment of gastrointestinal disorders, comprising administering the variant spasmolytic polypeptide of claim 10.

15. A method of preparing the HSP of claim 1 in at least 60% glycosylated form, wherein a host cell transformed with a DNA fragment encoding said HSP and capable of providing glycosylation of said HSP is cultured under conditions permitting production of said HSP and recovering the resulting spasmolytic polypeptide from the culture.

16. A method according to claim 15, wherein the host cell is a yeast cell or a filamentous fungus cell.

17. The method according to claim 16, wherein the host cell is a *Saccharomyces cerevisiae* or *Aspergillus oryzae*.

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
   ( A ) LENGTH: 106 amino acids
   ( B ) TYPE: amino acid
   ( C ) STRANDEDNESS: single
   ( D ) TOPOLOGY: linear ( i i ) MOLECULE TYPE: protein ( x i ) SEQUENCE DESCRIPTION: SEQ ID NO:1:

```
Glu  Lys  Pro  Ser  Pro  Cys  Gln  Cys  Ser  Arg  Leu  Ser  Pro  His  Asn  Arg
 1              5                        10                       15
```

```
        Thr  Asn  Cys  Gly  Phe  Pro  Gly  Ile  Thr  Ser  Asp  Gln  Cys  Phe  Asp  Asn
                       20                      25                      30

Gly  Cys  Cys  Phe  Asp  Ser  Ser  Val  Thr  Gly  Val  Pro  Trp  Cys  Phe  His
                       35                      40                      45

Pro  Leu  Pro  Lys  Gln  Glu  Ser  Asp  Gln  Cys  Val  Met  Glu  Val  Ser  Asp
                  50                      55                      60

Arg  Arg  Asn  Cys  Gly  Tyr  Pro  Gly  Ile  Ser  Pro  Glu  Glu  Cys  Ala  Ser
        65                      70                      75                           80

Arg  Lys  Cys  Cys  Phe  Ser  Asn  Phe  Ile  Phe  Glu  Val  Pro  Trp  Cys  Phe
                            85                      90                      95

Phe  Pro  Asn  Ser  Val  Glu  Asp  Cys  His  Tyr
                       100                     105
```

( 2 ) INFORMATION FOR SEQ ID NO:2:

( i ) SEQUENCE CHARACTERISTICS:
        ( A ) LENGTH: 563 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 77..553

( i x ) FEATURE:
        ( A ) NAME/KEY: sig_peptide
        ( B ) LOCATION: 77..235

( i x ) FEATURE:
        ( A ) NAME/KEY: mat_peptide
        ( B ) LOCATION: 236..553

( x i ) SEQUENCE DESCRIPTION: SEQ ID NO:2:

```
GAATTCCATT  CAAGAATAGT  TCAAACAAGA  AGATTACAAA  CTATCAATTT  CATACACAAT           60

ATAAACGACC  AAAAGA ATG  AAG  GCT  GTT  TTC  TTG  GTT  TTG  TCC  TTG  ATC        109
              Met  Lys  Ala  Val  Phe  Leu  Val  Leu  Ser  Leu  Ile
              -53            -50                           -45

GGA  TTC  TGC  TGG  GCC  CAA  CCA  GTC  ACT  GGC  GAT  GAA  TCA  TCT  GTT  GAG  157
Gly  Phe  Cys  Trp  Ala  Gln  Pro  Val  Thr  Gly  Asp  Glu  Ser  Ser  Val  Glu
          -40                      -35                           -30

ATT  CCG  GAA  GAG  TCT  CTG  ATC  ATC  GCT  GAA  AAC  ACC  ACT  TTG  GCT  AAC  205
Ile  Pro  Glu  Glu  Ser  Leu  Ile  Ile  Ala  Glu  Asn  Thr  Thr  Leu  Ala  Asn
     -25                      -20                      -15

GTC  GCC  ATG  GCT  GAG  AGA  TTG  GAG  AAG  AGA  GAG  AAA  CCC  TCC  CCC  TGC  253
Val  Ala  Met  Ala  Glu  Arg  Leu  Glu  Lys  Arg  Glu  Lys  Pro  Ser  Pro  Cys
-10                       -5                        1                  5

CAG  TGC  TCC  AGG  CTG  AGC  CCC  CAT  AAC  AGG  ACG  AAC  TGC  GGC  TTC  CCT  301
Gln  Cys  Ser  Arg  Leu  Ser  Pro  His  Asn  Arg  Thr  Asn  Cys  Gly  Phe  Pro
               10                       15                       20

GGA  ATC  ACC  AGT  GAC  CAG  TGT  TTT  GAC  AAT  GGA  TGC  TGT  TTC  GAC  TCC  349
Gly  Ile  Thr  Ser  Asp  Gln  Cys  Phe  Asp  Asn  Gly  Cys  Cys  Phe  Asp  Ser
               25                       30                       35

AGT  GTC  ACT  GGG  GTC  CCC  TGG  TGT  TTC  CAC  CCC  CTC  CCA  AAG  CAA  GAG  397
Ser  Val  Thr  Gly  Val  Pro  Trp  Cys  Phe  His  Pro  Leu  Pro  Lys  Gln  Glu
          40                       45                       50

TCG  GAT  CAG  TGC  GTC  ATG  GAG  GTC  TCA  GAC  AGA  AGA  AAC  TGT  GGC  TAC  445
Ser  Asp  Gln  Cys  Val  Met  Glu  Val  Ser  Asp  Arg  Arg  Asn  Cys  Gly  Tyr
55                       60                       65                       70

CCG  GGC  ATC  AGC  CCC  GAG  GAA  TGC  GCC  TCT  CGG  AAG  TGC  TGC  TTC  TCC  493
Pro  Gly  Ile  Ser  Pro  Glu  Glu  Cys  Ala  Ser  Arg  Lys  Cys  Cys  Phe  Ser
               75                       80                       85
```

```
AAC TTC ATC TTT GAA GTG CCA TGG TGC TTC TTC CCG AAC TCT GTG GAA        541
Asn Phe Ile Phe Glu Val Pro Trp Cys Phe Phe Pro Asn Ser Val Glu
            90                  95                  100

GAC TGC CAT TAC TAAGTCTAGA                                             563
Asp Cys His Tyr
        105
```

( 2 ) INFORMATION FOR SEQ ID NO:3:

( i ) SEQUENCE CHARACTERISTICS:
        ( A ) LENGTH: 159 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Met Lys Ala Val Phe Leu Val Leu Ser Leu Ile Gly Phe Cys Trp Ala
-53         -50                 -45                 -40

Gln Pro Val Thr Gly Asp Glu Ser Ser Val Glu Ile Pro Glu Glu Ser
        -35                 -30                 -25

Leu Ile Ile Ala Glu Asn Thr Thr Leu Ala Asn Val Ala Met Ala Glu
    -20                 -15                 -10

Arg Leu Glu Lys Arg Glu Lys Pro Ser Pro Cys Gln Cys Ser Arg Leu
 -5              1               5                   10

Ser Pro His Asn Arg Thr Asn Cys Gly Phe Pro Gly Ile Thr Ser Asp
            15                  20                  25

Gln Cys Phe Asp Asn Gly Cys Cys Phe Asp Ser Ser Val Thr Gly Val
        30                  35                  40

Pro Trp Cys Phe His Pro Leu Pro Lys Gln Glu Ser Asp Gln Cys Val
    45                  50                  55

Met Glu Val Ser Asp Arg Arg Asn Cys Gly Tyr Pro Gly Ile Ser Pro
 60              65                  70                      75

Glu Glu Cys Ala Ser Arg Lys Cys Cys Phe Ser Asn Phe Ile Phe Glu
            80                  85                  90

Val Pro Trp Cys Phe Phe Pro Asn Ser Val Glu Asp Cys His Tyr
            95                  100                 105
```

( 2 ) INFORMATION FOR SEQ ID NO:4:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

GGCTGAGCCC CCATAACAG                                                     19

( 2 ) INFORMATION FOR SEQ ID NO:5:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

TGGAAACACC AGGGGAC                                                      17

( 2 ) INFORMATION FOR SEQ ID NO:6:

( i ) SEQUENCE CHARACTERISTICS:
      ( A ) LENGTH: 31 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:6:

GAGAAACCCT CCCCCTGCCA GTGCTCCAGG C  31

( 2 ) INFORMATION FOR SEQ ID NO:7:

( i ) SEQUENCE CHARACTERISTICS:
      ( A ) LENGTH: 34 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:7:

TCAGCCTGGA GCACTGGCAG GGGGAGGGTT TCTC  34

( 2 ) INFORMATION FOR SEQ ID NO:8:

( i ) SEQUENCE CHARACTERISTICS:
      ( A ) LENGTH: 37 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:8:

GCTGAGAGAT TGGAGAAGAG AGAGAAACCC TCCCCCT  37

( 2 ) INFORMATION FOR SEQ ID NO:9:

( i ) SEQUENCE CHARACTERISTICS:
      ( A ) LENGTH: 17 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:9:

TGCGTCATGG AGGTCTC  17

( 2 ) INFORMATION FOR SEQ ID NO:10:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:10:

AGCACCATGG CACTTCAAAG  20

( 2 ) INFORMATION FOR SEQ ID NO:11:

( i ) SEQUENCE CHARACTERISTICS:

-continued (A) LENGTH: 60 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:11:

GTCCCTGGT GTTCCACCC CCTCCCAAAG CAAGAGTCGG ATCAGTGCGT CATGGAGGTC    60

(2) INFORMATION FOR SEQ ID NO:12:

(i) SEQUENCE CHARACTERISTICS:
(A) LENGTH: 60 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:12:

TGAGACCTCC ATGACGCACT GATCCGACTC TTGCTTTGGG AGGGGTGGA AACACCAGGG    60

(2) INFORMATION FOR SEQ ID NO:13:

(i) SEQUENCE CHARACTERISTICS:
(A) LENGTH: 46 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:13:

CATGGTGCTT CTTCCCGAAC TCTGTGGAAG ACTGCCATTA CTAAGT    46

(2) INFORMATION FOR SEQ ID NO:14:

(i) SEQUENCE CHARACTERISTICS:
(A) LENGTH: 46 base pairs
(B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:14:

CTAGACTTAG TAATGGCAGT CTTCCACAGA GTTCGGGAAG AAGCAC    46